United States Patent
Tsubouchi et al.

(10) Patent No.: US 10,492,904 B2
(45) Date of Patent: Dec. 3, 2019

(54) EQUIPMENT FOR PREPARING VALVE LEAFLET FROM MEMBRANE

(71) Applicant: Terumo Cardiovascular Systems Corporation, Ann Arbor, MI (US)

(72) Inventors: Takeshi Tsubouchi, Dexter, MI (US); Randal J. Kadykowski, South Lyon, MI (US)

(73) Assignee: TERUMO CARDIOVASCULAR SYSTEMS CORPORATION, Ann Arbor, MI (US)

( * ) Notice: Subject to any disclaimer, the term of this patent is extended or adjusted under 35 U.S.C. 154(b) by 330 days.

(21) Appl. No.: 15/606,678

(22) Filed: May 26, 2017

(65) Prior Publication Data

US 2017/0340439 A1 Nov. 30, 2017

Related U.S. Application Data

(60) Provisional application No. 62/342,483, filed on May 27, 2016.

(51) Int. Cl.
  *A61F 2/24* (2006.01)

(52) U.S. Cl.
  CPC .......... *A61F 2/2415* (2013.01); *A61F 2/2496* (2013.01)

(58) Field of Classification Search
  CPC ........ A61F 2/2415; A61F 2/2496; B26F 1/44; B26F 1/386; B26F 1/3813; B26F 1/3853
  USPC .......................................................... 600/36
  See application file for complete search history.

(56) References Cited

U.S. PATENT DOCUMENTS

| | | | |
|---|---|---|---|
| 2,612,123 A | 9/1952 | Nord | |
| 5,609,600 A * | 3/1997 | Love | A61B 17/32 606/167 |
| 6,129,758 A * | 10/2000 | Love | A61F 2/2415 623/2.11 |
| 6,454,799 B1 * | 9/2002 | Schreck | A61F 2/2418 623/2.18 |
| 6,461,382 B1 * | 10/2002 | Cao | A61F 2/2409 623/2.17 |
| 6,491,511 B1 * | 12/2002 | Duran | A61F 2/2415 425/394 |
| 6,497,713 B1 * | 12/2002 | Tompkins | A61F 2/2415 606/167 |
| 6,685,739 B2 * | 2/2004 | DiMatteo | A61F 2/2412 623/1.24 |

(Continued)

FOREIGN PATENT DOCUMENTS

WO 2015/141798 9/2015

*Primary Examiner* — Navin Natnithithadha
*Assistant Examiner* — Sunita Reddy
(74) *Attorney, Agent, or Firm* — Darryl Newell; MacMillan, Sobanski & Todd, LLC

(57) ABSTRACT

A device prepares leaflets for cardiovascular valve reconstruction from a pericardial tissue sheet harvested from a patient. A cutter is adapted to cut a predetermined pattern having a selected leaflet size. A tissue marker automatically aligned with the predetermined cutting pattern is configured to mark suture positions on the leaflet in response to placement of the cutter. Cutting of a leaflet from the tissue sheet and marking of suture positions on the leaflet are obtained concurrently. A set of such devices spanning a variety of leaflet sizes may be provided in a kit that results in an ability to quickly obtain a properly sized and marked leaflet for reconstruction.

8 Claims, 7 Drawing Sheets

(56) References Cited

U.S. PATENT DOCUMENTS

| | | | | |
|---|---|---|---|---|
| 7,462,156 B2* | 12/2008 | Mitrev | ............... | A61B 5/1072 |
| | | | | 33/512 |
| 9,044,246 B2 | 6/2015 | Goldfarb et al. | | |
| 9,050,180 B1* | 6/2015 | Kong | ............... | A61F 2/062 |
| 9,331,328 B2* | 5/2016 | Eberhardt | ............ | A61F 2/2415 |
| 9,414,920 B2* | 8/2016 | Ozaki | ............... | A61F 2/2415 |
| 9,474,602 B2* | 10/2016 | Umezu | ............... | A61F 2/2412 |
| 2002/0091441 A1* | 7/2002 | Guzik | ............... | A61F 2/2415 |
| | | | | 623/2.13 |
| 2007/0251364 A1* | 11/2007 | Blumle | ............... | B26D 7/018 |
| | | | | 83/100 |
| 2010/0018447 A1* | 1/2010 | Holecek | ............ | A61F 2/2415 |
| | | | | 112/217.1 |
| 2010/0023119 A1* | 1/2010 | Yeo | ............... | A61F 2/2415 |
| | | | | 623/2.14 |
| 2011/0251598 A1* | 10/2011 | Ozaki | ............... | A61F 2/2415 |
| | | | | 606/1 |
| 2011/0307055 A1* | 12/2011 | Goldfarb | ............ | A61B 17/0469 |
| | | | | 623/2.11 |
| 2012/0035720 A1 | 2/2012 | Cali et al. | | |
| 2013/0013058 A1* | 1/2013 | Umezu | ............... | A61F 2/2412 |
| | | | | 623/2.12 |
| 2013/0055941 A1* | 3/2013 | Holecek | ............ | A61F 2/2415 |
| | | | | 112/475.01 |
| 2013/0089555 A1 | 4/2013 | Gregg | | |
| 2016/0221206 A1* | 8/2016 | Jeske | ............... | B26F 1/40 |

* cited by examiner

EQUIPMENT FOR PREPARING VALVE LEAFLET FROM MEMBRANE

CROSS REFERENCE TO RELATED APPLICATIONS

This application claims priority to U.S. provisional application 62/342,483, filed on May 27, 2016, which is incorporated herein by reference in its entirety.

STATEMENT REGARDING FEDERALLY SPONSORED RESEARCH

Not Applicable.

BACKGROUND OF THE INVENTION

The present invention relates in general to marking and cutting a heart valve leaflet from a pericardium membrane for use in valve repair/reconstruction, and, more specifically, to devices and systems for simultaneously marking and cutting a valve leaflet with improved accuracy and shortened operating times.

One type of heart surgery relates to heart valve repair or replacement. For a patient with a damaged valve leaflet (e.g., in a bicuspid or tricuspid valve), there is a surgical technique for repairing the valve leaflet using the patient's own pericardium tissue, bovine tissue, or a synthetic material. A man-made synthetic valve has good durability but requires continuous use of an anti-coagulate drug. A valve leaflet reconstruction operation using pericardium tissue removed from the patient is becoming a preferred technique. A thin sheet of pericardium tissue harvested from the patent must be cut and shaped according to the required size of the replaced leaflet. The cut leaflet is then sewn into the original position of the diseased leaflet. This therapy appears to have longer life compared to a bovine tissue valve, and it is generally safe from rejection since this therapy uses the patient's own tissue.

More specifically, the procedure for valve leaflet repair may include the following steps. Circulatory support incisions are made and a perfusion system (i.e., heart lung machine) is connected. The target heart valve (e.g., aortic valve) is then exposed. A thin sheet of pericardium tissue is excised and prepared by treatment with known chemicals. The damaged valve leaflet is trimmed away. A sizing tool is used in order to measure the site (e.g., valve width) to which the new leaflet will be attached. The processed pericardium tissue is placed on a backing plate. Using a template corresponding to the measured size and a marking pen, the desired size and shape for a replacement leaflet is stenciled onto the tissue sheet. The locations (e.g. up to 15 dots) for forming individual sutures may also be marked. Using scissors, the stenciled leaflet is manually cut and trimmed from the tissue sheet. The leaflet is sutured onto the valve annulus and the leaflet commissures are sutured.

During the time that the cut and trim tasks are performed, the heart is stopped and the patient is supported by external circulation using oxygenator and blood pump. This has unfavorable effects on the body, so the duration needs to be minimized. Thus, it would be desirable to minimize valve leaflet preparation time while obtaining more accurately shaped leaflets, thereby contributing to better outcomes of the therapy.

SUMMARY OF THE INVENTION

The invention introduces various devices wherein each device is itself capable of both cutting a desired leaflet size and marking suturing locations in one user action. In one example, a device for preparing leaflets for cardiovascular valve reconstruction resembles a stamper or embosser with a "cookie cutter" blade. The device combines a cutting edge with a tissue marker, wherein cutting of a leaflet from a membrane is obtained simultaneously with marking suture positions on the leaflet.

DETAILED DESCRIPTION OF PREFERRED EMBODIMENTS

Figure 1:
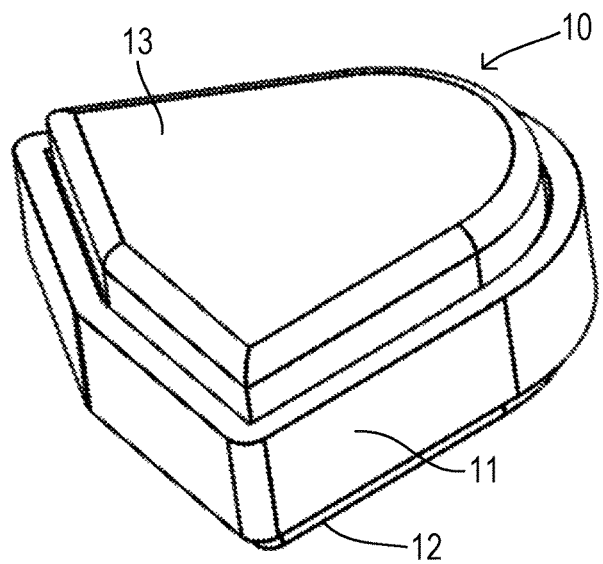
FIGS. 1-3 are perspective views of a cutting/marking device according to a first embodiment of the invention.
Figure 2:
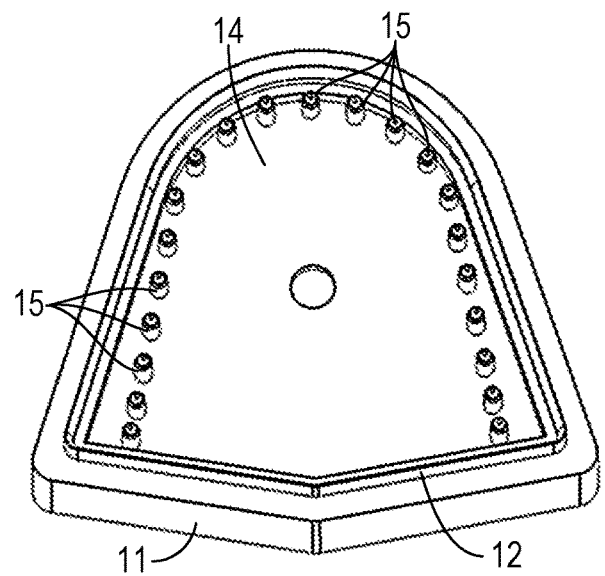
Figure 3:
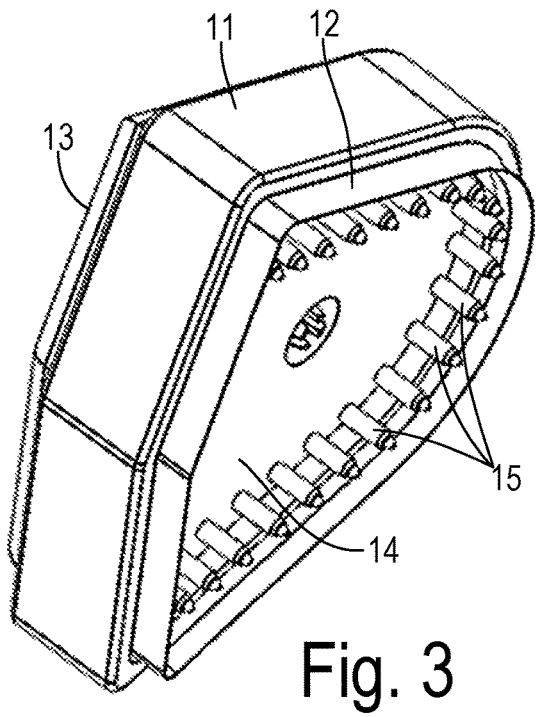

A first embodiment of a "cookie cutter" type of leaflet cutting and marking device 10 is shown in FIGS. 1-7. Referring to FIGS. 1-3, a base plate 11 provides a frame for supporting a cutting blade 12 on a bottom side. Preferably, base plate 11 generally conforms to and is slightly larger than a desired leaflet profile. Cutting blade 12 provides a cutting edge following a precisely configured cutting pattern according to a selected leaflet dimension. The particular size for which device 10 is configured may preferably be labeled on the device so that a kit having a plurality of differently sized cutting devices can be bundled to support a surgical procedure. Base plate 11 has an upper cavity receiving a plunger 13 which is slidably mounted for upward and downward movement within the upper cavity of base plate 11. Base plate 11 has a bottom wall 14 with appropriately placed apertures receiving a plurality of ink applicators 15 which are extendable under control of plunger 13.

Figure 4:
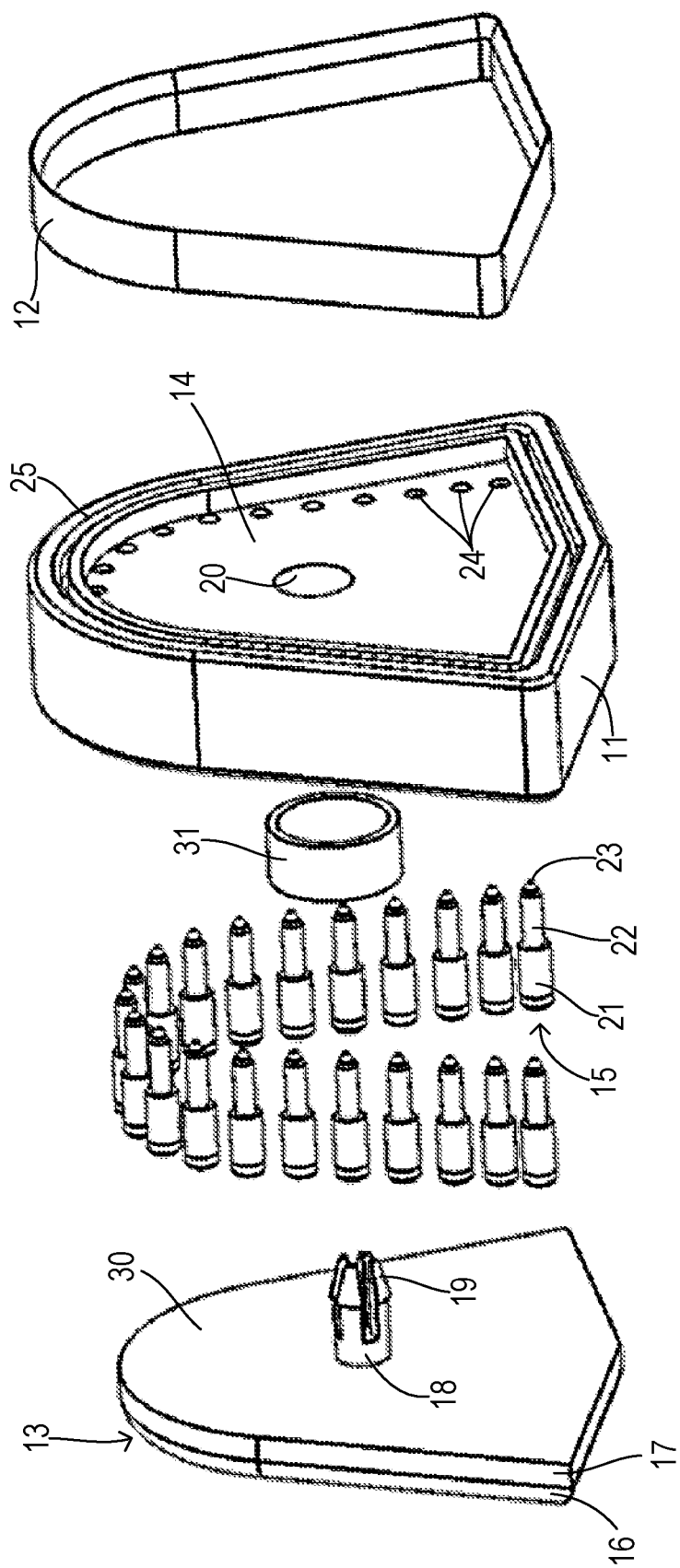
FIG. 4 is an exploded view of the device of FIG. 1.

Referring to FIG. 4, base plate 11 includes a bottom groove 25 which fixedly mounts cutting blade 12. Bottom wall 14 of base plate 11 includes a plurality of apertures 24 each arranged to receive a respective one of ink applicators 15. Each ink applicator 15 includes a spring-loaded base 21, pen body 22, and marking tip 23. Apertures 24 are sized to accommodate pen bodies 22. Spring bases 21 are arranged to abut a thrust surface 30 on plunger 13. A bias member (e.g., spring) 31 is disposed between wall 14 and thrust surface 30 in order to urge surface 30 into an upward position wherein applicator tips 23 are retracted to a position farthest away from the cutting side. Plunger 13 may preferably include a rigid top section 16 and a resilient bottom section or layer 17. Resilient section 17 cushions the interface with ink applicators 15 and may be comprised of a rubber sheet. Rigid top section 16 is integrally formed with a mounting shaft 18 extending toward a bore 20 in wall 14.

Latching tabs 19 on a bottom end of shaft 18 may interlock with the latching surface in bore 20.

Figure 5:
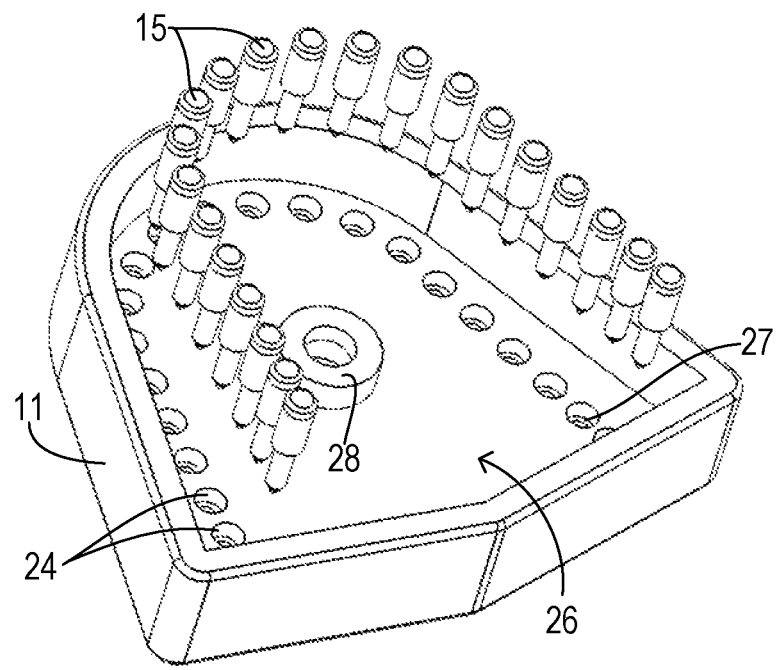
FIG. 5 is an exploded view of the base plate and ink applicators.
Figure 6:
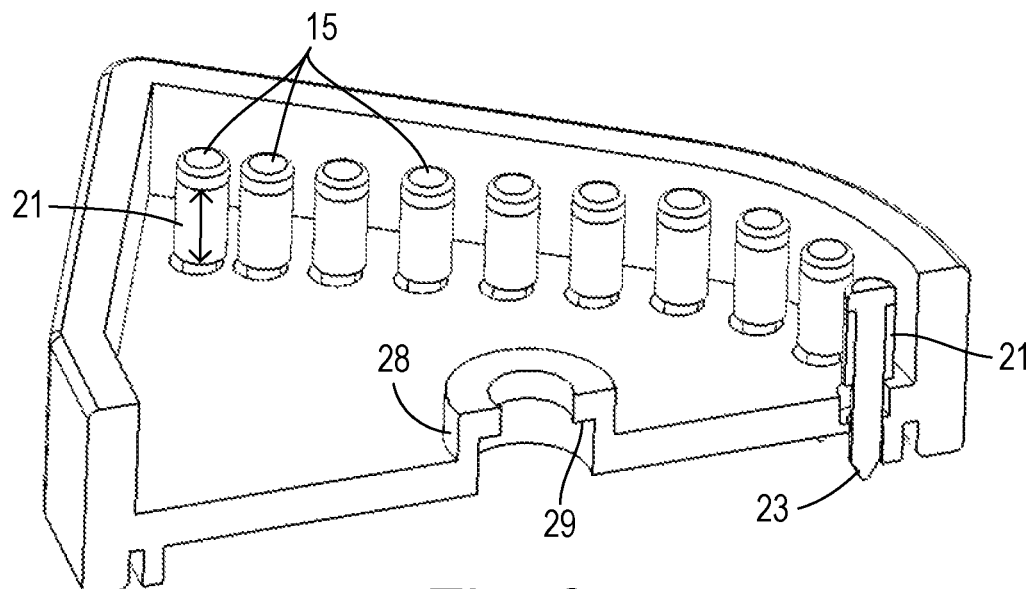
FIG. 6 is a partial cross-sectional view of the base plate and ink applicators.
Figure 7:
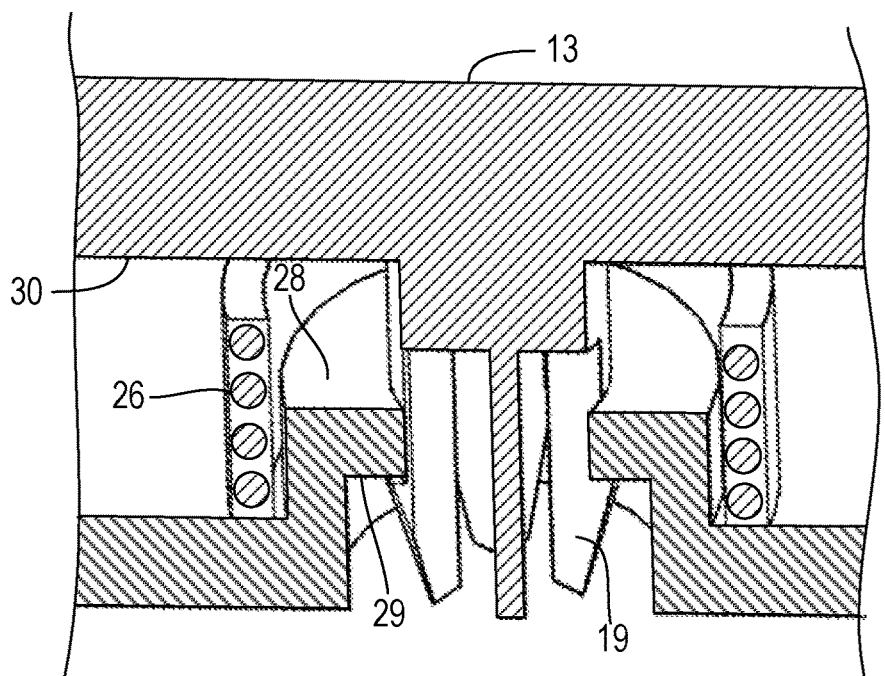
FIG. 7 is a cross-sectional view showing the mounting of the plunger and the base plate in greater detail.

Referring to FIG. 5, upper cavity 26 of base plate 11 receives ink applicators 15. Each aperture 24 includes a shoulder 27 to retain spring bases 21 of ink applicators 15 within cavity 26 by interference between spring bases 21 and shoulders 27. A collar 28 is adapted to align and retain one end of spring 31 (FIG. 4) and to provide an internal latching surface 29 (FIG. 6) for receiving latching tabs 19 (FIG. 4). The arrangement for slidably retaining plunger 13 in alignment with collar 28 is shown in greater detail in FIG. 7.

Figure 8A:
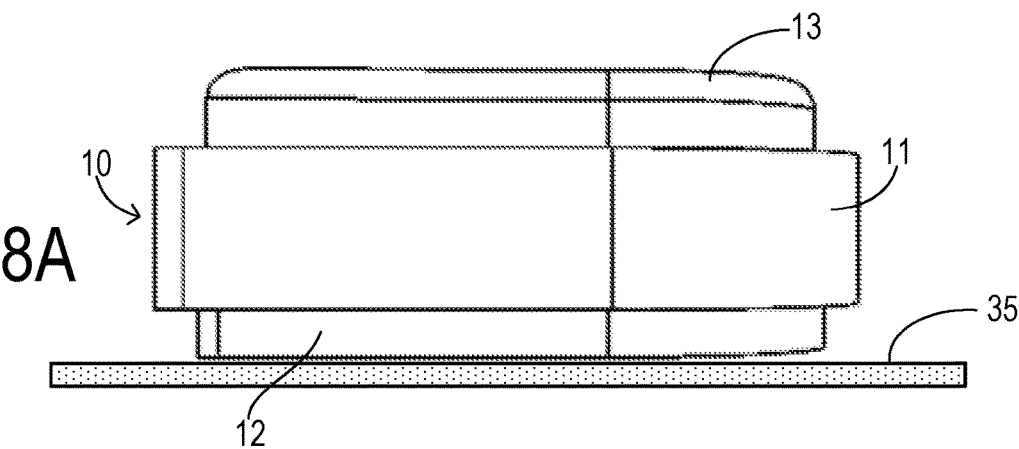
FIGS. 8A, 8B, and 8C show a sequence of concurrently cutting and marking a leaflet using the device of FIG. 1.
Figure 8B:
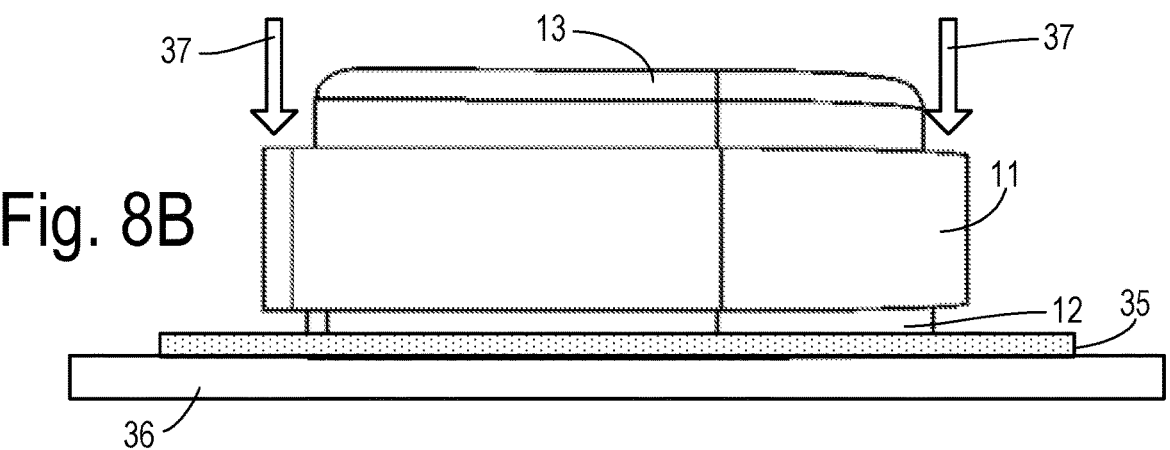
Figure 8C:
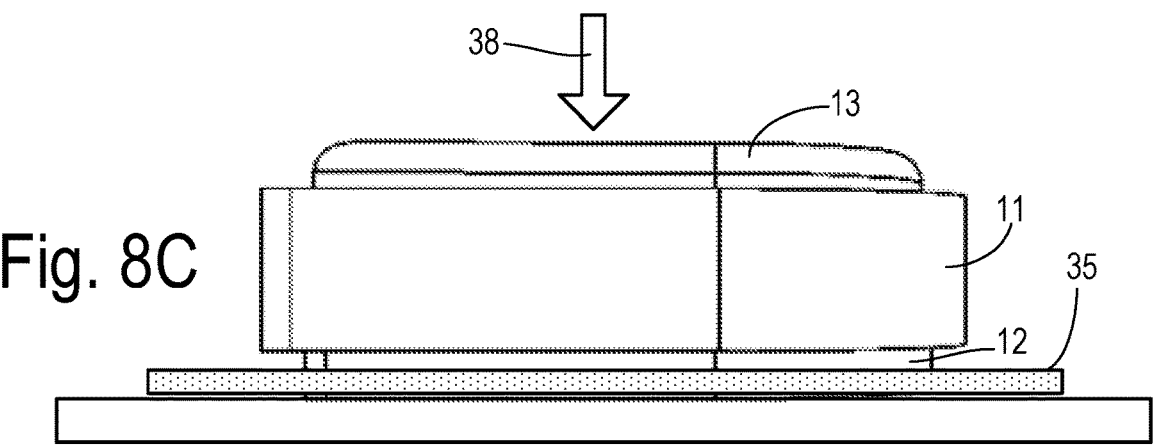

Preparation of a leaflet using the present invention is shown in FIGS. 8A-8C. In FIG. 8A, a pericardial membrane sheet 35 is first prepared and a surgeon measures a patient's aortic structures to determine a desired leaflet size. A device 10 matching the measured dimensions for the desired leaflet size is selected and brought into contact with sheet 35. As shown in FIG. 8B, sheet 35 and device 10 are preferably arranged on top of a rigid backing plate 36. By manually applying a pressing force 37 onto base plate 11 (i.e., without applying pressure to plunger 13), cutting blade 12 penetrates sheet 35 thereby quickly and precisely cutting a leaflet of the desired dimensions. Without removing device 10, marking of the corresponding suture positions is concurrently performed as shown in FIG. 8C using a downward pressing force 38 against plunger 13. As a result, the ink applicators are moved against the spring bias forces (created by the main bias member and the individual ink applicator spring bases) until contacting the cut leaflet and marking the desired suture positions defined by the placement of the ink applicators.

Figure 9:
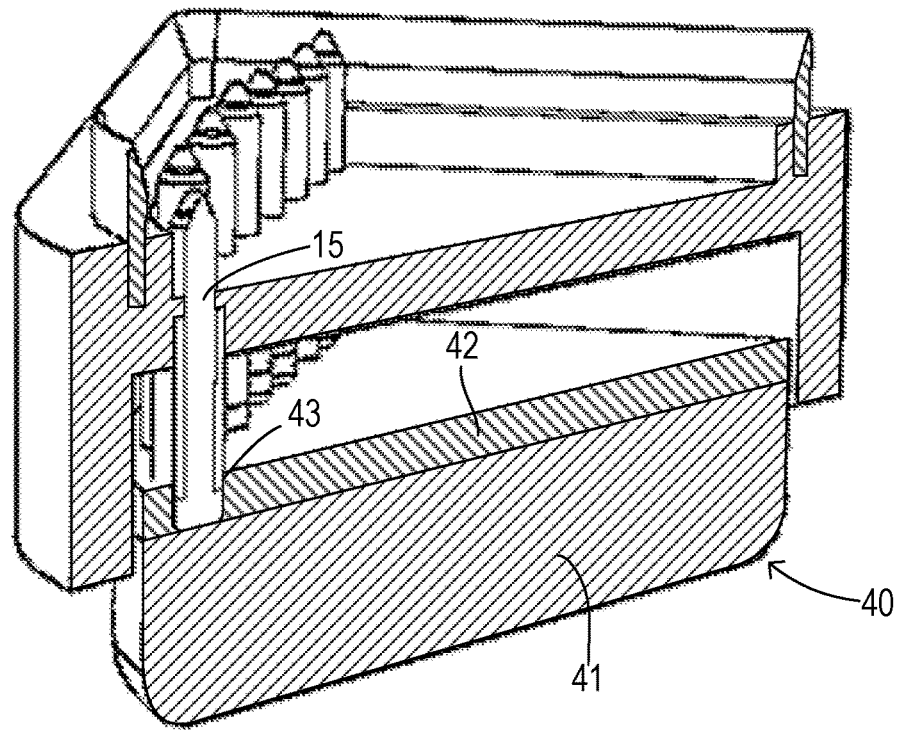
FIG. 9 is a cross section showing an alternative embodiment of a cutting/marking device.

As shown in FIG. 9, a plunger 40 may have a top section 41 and resilient bottom layer 42. In order to improve alignment of ink applicators 15, a socket 43 may be formed as a depression or hole within layer 42 having a diameter to receive one end of a respective ink applicator.

Figure 10:
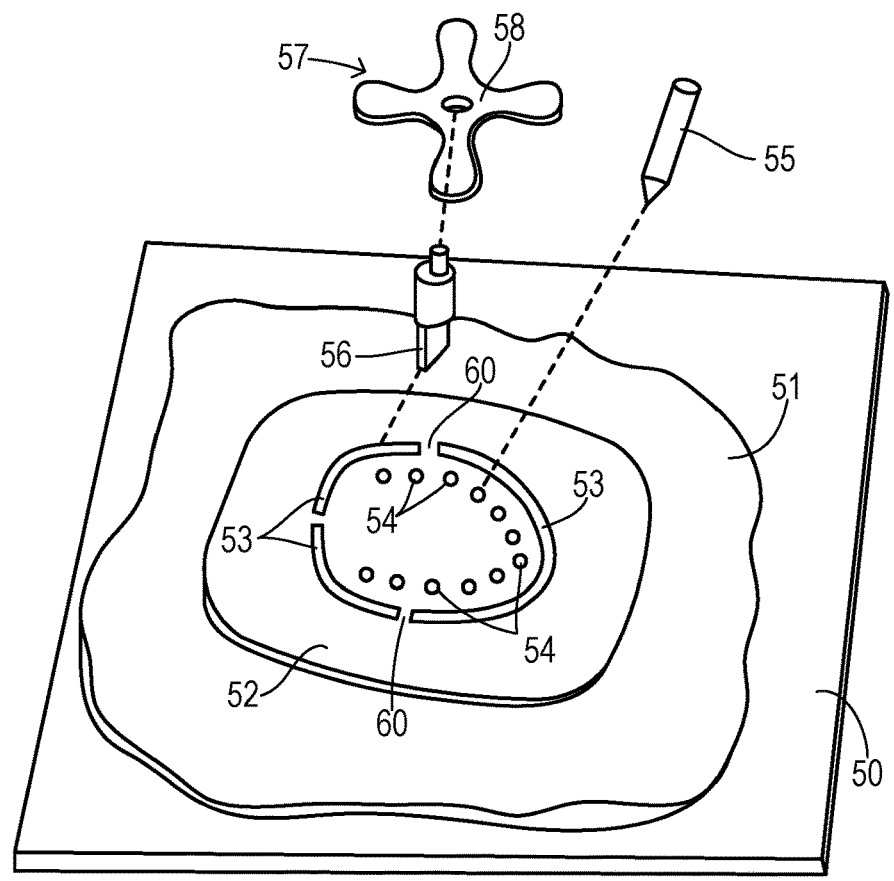
FIG. 10 is a perspective view of another embodiment including a cutting and marking stencil.

In an embodiment shown in FIG. 10, a support plate 50 receives a pericardial sheet or membrane 51 harvested from a patient. A stencil plate 52 (e.g., comprised of a thin, biocompatible metal plate) has a series of grooves or slots 53 following an outline of a leaflet of a predetermined size. A surgical setting would be equipped with a plurality of stencil plates configured for a variety of leaflet sizes so that one matching a measured dimension can be selected. Stencil plate 52 further includes a series of marking holes 54 penetrating stencil plate 52 and having a diameter sufficient to accommodate a marking pen 55. Grooves 53 have a width adapted to accommodate a cutting blade 56 of a cutting tool 57. Blade 56 is mounted to a handle 58 so that an outline of a desired leaflet can be manually cut while pressing stencil plate 52 against sheet 51. Connecting bridges 60 may be needed which interrupt grooves 53, but corresponding cuts beneath bridges 60 can be easily made in sheet 51 after removing stencil plate 52. In an alternative embodiment, grooves and marking holes for differently sized leaflets can be provided on a single stencil plate provided that the included features (i.e., edges and holes) do not overlap.

Figure 11:
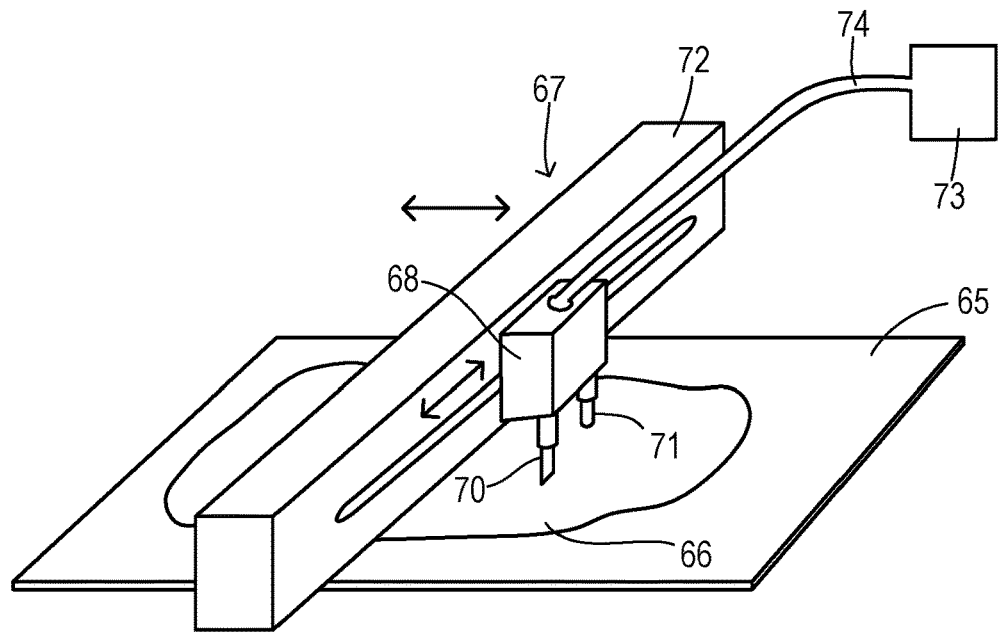
FIG. 11 is a perspective view of another embodiment including a motion control table.

In an embodiment in FIG. 11, a support plate 65 receives a pericardial sheet or membrane 66 harvested from a patient. An X-Y motion control mechanism 67 is provided having a carriage 68 supporting a cutting blade 70 and a marking pen 71 which are vertically extendable from carriage 68 in response to a programmable controller (not shown). Carriage 68 is slidably mounted on a movable arm 72 such that servo mechanisms can translate the position of blade 70 and pen 71 to follow any desired pattern to create (i.e., cut and mark) a desired leaflet. Pen 71 may be comprised of an ink jet head connected to an ink reservoir 73 by a conduit 74. The controller may include a library of pre-defined patterns according to a variety of desirable leaflet shapes and sizes to be selected according to the needs of a particular patient.

Figure 12:
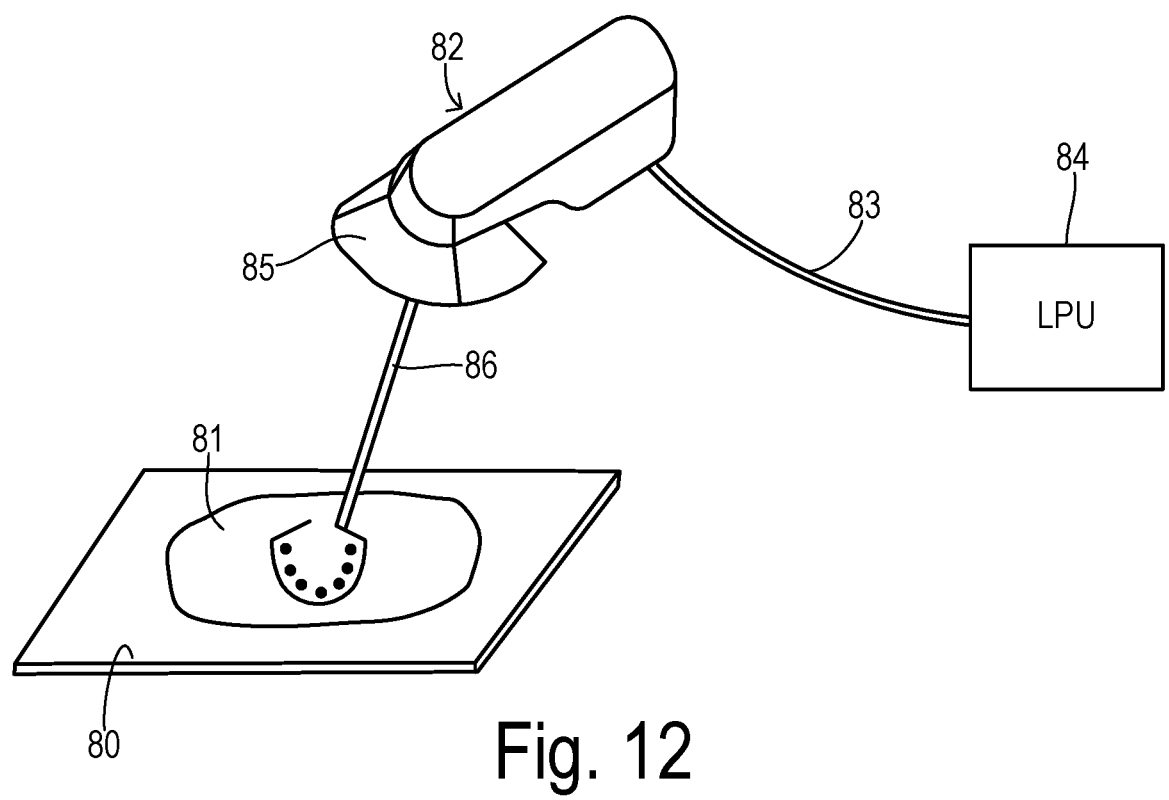
FIG. 12 is a perspective view of another embodiment including a laser marking and cutting system.

In an embodiment in FIG. 12, a support plate 80 receives a pericardial sheet or membrane 81 harvested from a patient. Cutting and marking to form a desired leaflet from sheet 81 is performed using a laser scanning device 82 connected by a laser fiber 83 to a laser power unit (LPU) 84 (e.g., an Nd-YAG laser). Scanning device 82 may comprise a polygon mirror unit 85 with motion control to scan a laser beam 86 according to pre-programmed patterns for different sizes of leaflets. LPU 84 provides two different power levels, wherein a higher power level is used while scanning a leaflet edge in order to cut (i.e., ablate) the leaflet and a lower power level (reduced amplitude or shortened time pulse) is used while positioning laser beam 86 at the locations of the suture markers in order to create a visible surface burn without significant penetration. In an alternate embodiment, the laser projection lens could be mounted on an X-Y motion control mechanism of the type shown in FIG. 11 in order to scan the laser beam along the desired paths.

What is claimed is:

1. A device for preparing leaflets for cardiovascular valve reconstruction from a tissue sheet, comprising:
    a cutter configured to cut a predetermined cutting pattern having a selected leaflet size;
    a base plate generally conforming to a desired leaflet profile, wherein the base plate has a bottom groove according to the predetermined pattern, wherein the cutter is comprised of a cutting blade mounted in the bottom groove, wherein the base plate has a plurality of apertures according to the suture positions, and
    a plunger slidably mounted to the base plate having a thrust surface arranged to press the ink applicators to downwardly extend through the apertures;
    a bias member urging the thrust surface toward an upward position; and
    a tissue marker comprised of a plurality of ink applicators each mounted in a respective aperture and automatically aligned with the predetermined cutting pattern to mark suture positions on a prepared leaflet in response to placement of the cutter;
    wherein cutting of the prepared leaflet from the tissue sheet and marking of suture positions on the leaflet are obtained concurrently;
    wherein manually pressing the base plate against the tissue sheet cuts the predetermined cutting pattern of the cutting blade and manually pressing the plunger marks the suture positions while a cut leaflet remains within the cutting blade.

2. The device of claim 1, wherein each ink applicator includes a bias spring that retracts the ink applicator against the thrust surface in the upward position.

3. The device of claim 1, wherein the plunger comprises a rigid top section and a resilient bottom section providing the thrust surface.

4. The device of claim 3, wherein the rigid top section includes a mounting shaft slidably attached to the base plate.

5. A device for preparing leaflets cut from a tissue sheet for cardiovascular valve reconstruction, comprising:
    a base plate generally conforming to a desired leaflet size, wherein the base plate has a bottom groove according to a predetermined cutting pattern corresponding to the desired leaflet size, and wherein the base plate has a plurality of apertures according to a pattern of predetermined suture positions for the desired leaflet size; a cutting blade mounted in the bottom groove; a plurality of ink applicators each mounted in a respective aperture; a plunger slidably mounted to the base plate having a thrust surface arranged to press the ink applicators to downwardly extend through the apertures; and a bias member urging the thrust surface toward an upward position;

wherein manually pressing the base plate against the tissue sheet cuts the predetermined cutting pattern of the cutting blade through the tissue sheet to cut the prepared leaflet and manually pressing the plunger marks the pattern of predetermined suture positions while the prepared leaflet remains within the cutting blade.

6. The device of claim 5, wherein each ink applicator includes a bias spring that retracts the ink applicator against the thrust surface in the upward position.

7. The device of claim 5, wherein the plunger comprises a rigid top section and a resilient bottom section providing the thrust surface.

8. The device of claim 7, wherein the rigid top section includes a mounting shaft slidably attached to the base plate.

* * * * *